United States Patent
Nestenborg

(10) Patent No.: US 7,122,025 B1
(45) Date of Patent: Oct. 17, 2006

(54) RECTAL INSERTION DEVICE

(75) Inventor: Daniel Nestenborg, Mölndal (SE)

(73) Assignee: Astra Tech AB, Molndal (SE)

( * ) Notice: Subject to any disclaimer, the term of this patent is extended or adjusted under 35 U.S.C. 154(b) by 664 days.

(21) Appl. No.: 10/088,555

(22) PCT Filed: Sep. 28, 2000

(86) PCT No.: PCT/SE00/01871

§ 371 (c)(1),
(2), (4) Date: Jun. 5, 2002

(87) PCT Pub. No.: WO01/24743

PCT Pub. Date: Apr. 12, 2001

(30) Foreign Application Priority Data

Oct. 6, 1999 (SE) .................................. 9903613

(51) Int. Cl.
*A61M 1/00* (2006.01)
*A61M 25/00* (2006.01)

(52) U.S. Cl. ....................... 604/540; 604/276

(58) Field of Classification Search ............. 604/275, 604/276, 327, 328, 540–544
See application file for complete search history.

(56) References Cited

U.S. PATENT DOCUMENTS

| 4,325,370 A | 4/1982 | Young |
| 4,333,460 A | 6/1982 | Miller |
| 4,709,705 A | 12/1987 | Truglio |
| 5,217,439 A | 6/1993 | McClusky |

FOREIGN PATENT DOCUMENTS

| AU | 13954/20 | 1/1920 |
| AU | 106028 | 12/1938 |
| AU | 18442/83 | 3/1984 |
| DE | 44 36 796 A1 | 4/1996 |
| EP | 0 109 897 A1 | 5/1984 |
| EP | 0 274 415 A3 | 7/1988 |
| GB | 2 251 384 A | 7/1992 |
| GB | 2 224 212 A | 5/1995 |
| WO | 99/30652 A1 | 6/1999 |

*Primary Examiner*—Tatyana Zalukaeva
*Assistant Examiner*—Linh Truong
(74) *Attorney, Agent, or Firm*—Birch, Stewart, Kolasch & Birch, LLP

(57) ABSTRACT

A rectal insertion device (1) for the treatment of disorders of the digestive tract of a human or animal patient having a body (3, 5) comprises a forward section (8) which in an operative position of the device is disposed in the anal canal of the patient, a first passageway (9) which extends forward opening (11) in the forward section, a rearward section (3) having a forward end which in the operative position is disposed extra-coporeally and a second passageway (4) which extends rearwardly in the device from a second forward opening (7) in the forward end of the rearward section. The second passageway acts to catch faeces discharged from the anal canal not caught in the first passageway.

27 Claims, 2 Drawing Sheets

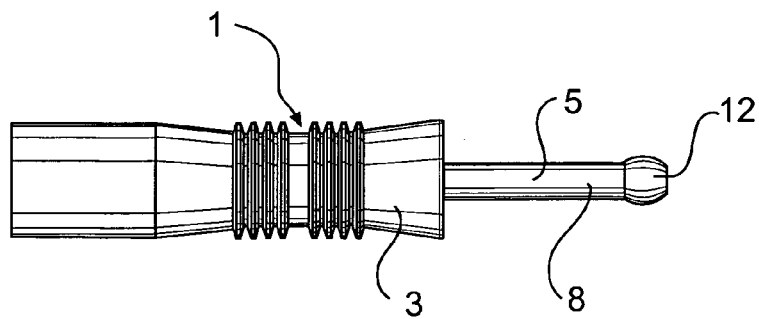
Fig. 1
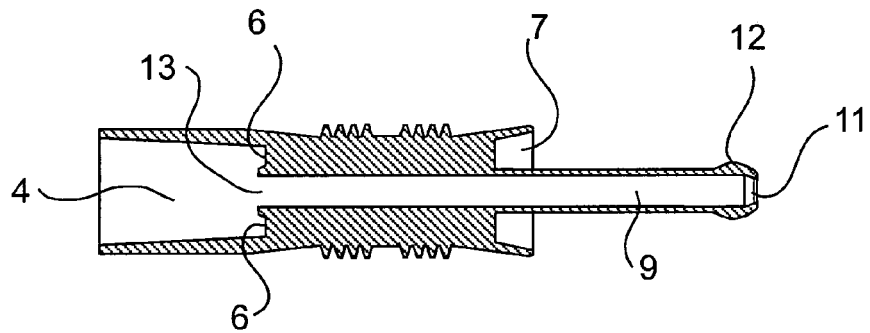
Fig. 2a
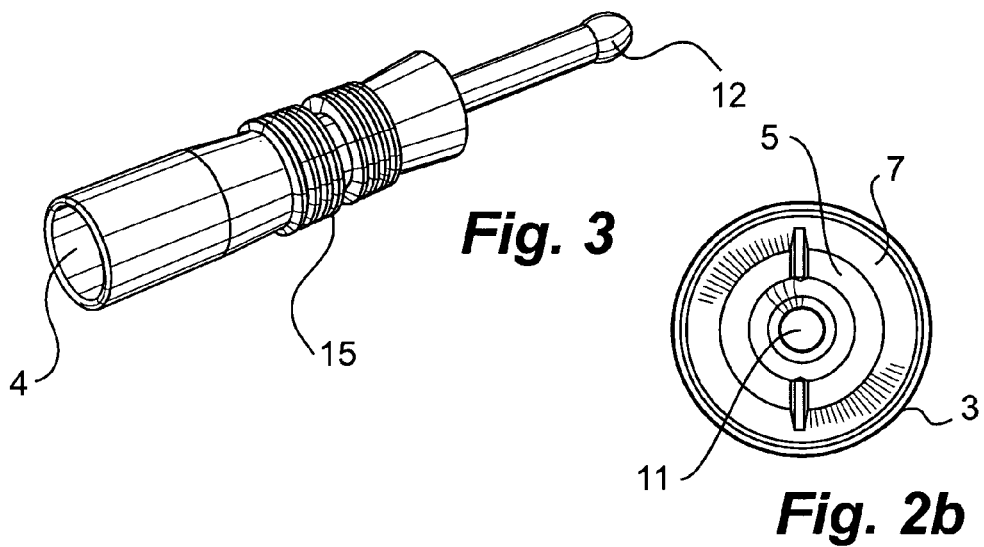
Fig. 3
Fig. 2b

RECTAL INSERTION DEVICE

This application is the national phase under 35 U.S.C. § 371 of PCT International Application No. PCT/SE00/01871 which has an International filing date of Sep. 28, 2000, which designated the United States of America.

FIELD OF THE INVENTION

The present invention relates to a rectal insertion device for the treatment of disorders of the digestive tract of a human or animal patient, said device comprising a forward section which in an operative position of the device is disposed in the anal canal of the patient and a first passageway which extends rearwardly in the device from a first forward opening in the forward section. The invention further relates to a method for treatment of disorders of the digestive tract of a human or animal patient.

Disorders of the digestive tract which may be treated with rectal insertion devices of the type defined are colic, including infantile colic, haemorrhoids, constipation, gas and piles.

BACKGROUND AND SUMMARY OF THE INVENTION

WO 99/30652 by the same applicant discloses a rectal insertion device of the above-mentioned type, wherein the first passageway is provided to channel faeces and gastrointestinal gases released on insertion of the forward section into the anal canal into a collection bag. A drawback of this known device is that some of the released faeces, however, may be ejected over the outer surface of the forward section instead of through the first passageway and thus not be collected in the bag. This also renders the device difficult to use efficiently.

Many of the known devices for treating disorders of the digestive tract are also difficult and expensive to produce. Further, they could also be dangerous to use, since a to deep insertion into the anal canal could result in severe injuries to the intestine. This risk is especially high when treating infants.

The aim of the present invention is to provide a rectal insertion device of the above-mentioned type which alleviates at least some of the drawbacks of the prior art devices.

According to a first aspect of the present invention there is provided a rectal insertion device of the above-mentioned type in which there is provided a rearward section having a forward end which in the operative position is disposed extra-corporeally and a second passageway which extends rearwardly in the device from a second forward opening in the forward end of the rearward section. The second passageway acts to catch faeces discharged from the anal canal not caught in the first passageway.

According to a second aspect of the invention there is provided a rectal insertion device of the above-mentioned type in which there is provided a rearward section having a forward end presenting a second forward opening intended to be extra-corporeally in use, said second forward opening being arranged rearwardly from the first forward opening. The rearward section preferably comprises a rearwardly extending, second passageway being connected to the second opening.

The device according to the invention is easy to use and produce. Further, it comprises means for collecting the released faeces ejected over the outer surface of the forward section instead of through the first passageway.

In an embodiment of the invention the forward end of the rearward section abuts with the anus of the patient in an operative position of the device. Further it is preferred that the forward end of the rearward section has a transverse dimension greater than the transverse dimension of the forward section and the forward section extends forwardly from the forward end of the rearward section. Hereby, the depth of insertion could be precisely controlled, enabling the sphincter muscles to be stimulated if need be and gastrointestinal gases and faeces to be discharged. The abutment also sees to that a too deep insertion of the forward section into the anal canal is avoided. Hereby, the device could be used without the risk of causing any harmful injuries to the user.

In an embodiment of the invention the forward section and rearward sections are co-axially arranged. It is also preferred that second forward opening is an annulus formed around the forward section. Hereby, the device need not have a specific rotational position in use, which makes the device self-explanatory and easier to use.

In an embodiment of the invention the first passageway communicates with the second passageway. Hereby, discharged faeces and gases will be brought together, and could thereafter emanate from the same output opening, making it easier to take care of.

In an embodiment of the invention the second passageway has a rearward opening in the rearward section.

In an embodiment of the invention the rearward section of the device comprises a tube element having an open-ended axial lumen.

In an embodiment of the invention the device comprises an elongate shaft having a forward portion which presents the forward section of the device and a rearward portion which extends rearwardly from the forward portion into the lumen of the tube element and through which the first passageway extends.

In an embodiment of the invention the first passageway has a rearward opening in the rearward portion of the elongate shaft.

In an embodiment of the invention the rearward portion of the elongate shaft is spaced from, and attached to, the wall of the lumen through one or more ribs.

In an embodiment of the invention the forward section is made more flexible than the rearward section in order to form a non-harmful and convenient insertion section, while the more rigid rearward section may form a convenient gripping section.

The invention also relates to a method for treating disorders of the digestive tract of a human or animal patient, comprising the step of at least one time inserting a forward section of a device into the anal canal of the patient, said forward section comprising a first passageway which extends rearwardly in the device from a first forward opening in the forward section characterised in that the device is inserted into the anal canal into a position where a rearward section of the device abuts the anus with a forward end, said rearward section comprising a second passageway which extends rearwardly in the device from a second forward opening in the forward end of the rearward section.

Other benefits and advantageous features of the invention will be apparent from the following description and claims.

An exemplary embodiment of the invention will now be described with reference to the accompanying Figures of drawings.

BRIEF DESCRIPTION OF THE DRAWINGS

FIG. 1 is a side view of a rectal insertion device in accordance with a first embodiment of the invention.

FIG. 2a is a cross-sectional side view of the rectal insertion device of FIG. 1.

FIG. 2b is an elevated view of the rectal insertion device in FIG. 1.

FIG. 3 is a perspective view of the rectal insertion device of FIG. 1.

DESCRIPTION OF PREFERRED EMBODIMENTS

Figure 5:
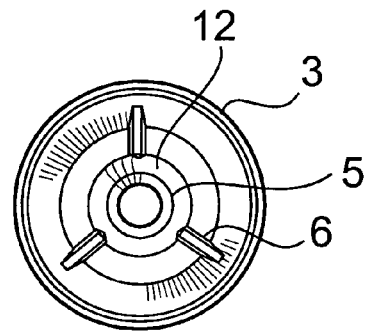
FIG. 5 is an elevated view of the rectal insertion device of FIG. 4.

In the FIGS. 1–3 of drawings there is shown a rectal insertion device 1 for treating disorders of the digestive tract of a human patient such as colic in accordance with a first embodiment of the invention. In the FIGS. 4–7 alternative embodiments are illustrated. However, someone skilled in the art would appreciate that the features of the different embodiments may be combined in different ways, and when nothing else is stated different aspects of certain features are regarded as mutually exchangeable.

The device is preferably injection moulded from a polyether block amide, such as Pebax™ (Elf Atochem).

The device 1 has a body 3,5 comprising a rearward section comprising a tube element 3 having a second passageway, preferably comprising an open-ended axial lumen 4, and an elongate shaft 5 which is mounted in the lumen 4, preferably co-axially. In a preferred embodiment the shaft is connected to the tube element through rib elements 6 so as to define an annulus 7 between the elongate shaft 5 and the lumen wall.

In the illustrated embodiments of the invention, the lumen 4 of the tube 3 ends axially in the rearward end. However, it is also conceivable to have a rearward opening debouching radially, or at least partly in a radial direction. To this end, one or several lateral openings could be arranged on the walls of the rearward section, ahead of a preferably sealed rearward end. It is also conceivable to let the tube be curved, in which case the rearward opening debouches axially, but not rearwardly. By providing an output opening for discharged faeces and gases not debauching rearwardly, it is avoided that discharge products are ejected onto the person manoeuvring the device.

The tube element is preferably substantially circular in cross-section, as is illustrated in the embodiments according to FIGS. 1–6. However, other shapes are also conceivable, e.g. oval, such as elliptic or eye-shaped, as is illustrated by the embodiment according to FIG. 7. Such a shape makes the device easier to bring into abutment with the anus of the patient.

Figure 6:
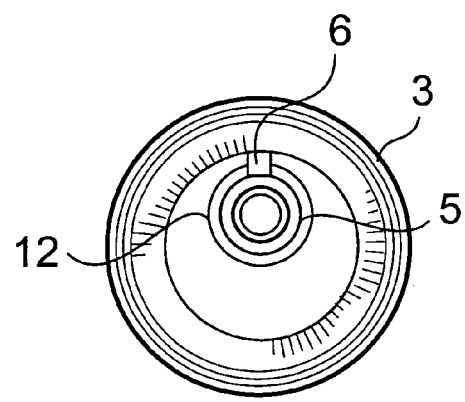
FIG. 6 is an elevated view of a rectal insertion device according to a third embodiment of the invention.
Figure 7:
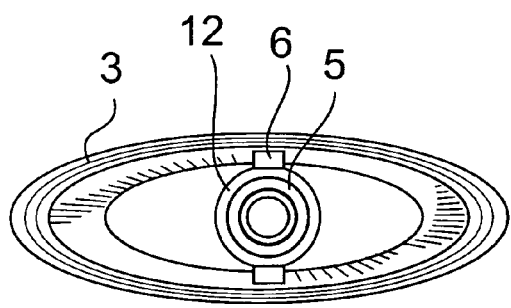
FIG. 7 is an elevated view of a rectal insertion device according to a fourth embodiment of the invention.
Figure 4:
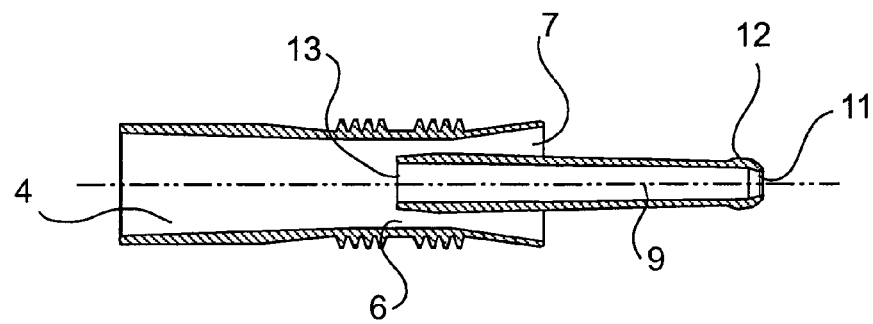
FIG. 4 is a cross-sectional side view of a rectal insertion device according to a second embodiment of the invention.

In FIGS. 1–3 the connection between the shaft 5 and the tube element 3 comprises two axially elongated rib elements 6. However, it is also possible to use one single rib element instead, or to use three or more rib elements, as is the case in the embodiment illustrated in FIGS. 4 and 5. Other alternative ways of obtaining such a connection are also possible. For example, the shaft 5 may be radially displaced relative to the tube element 3, whereby it could be directly connected to the inner wall of the tube element, as illustrated in FIG. 6. Further, the ribs need not be axially elongated, but could instead be arranged axially displaced.

As can be seen, the elongate shaft 5 is divided into a rearward portion which is disposed inside the lumen 4 of the tube element 3 and a forward portion 8 which protrudes from the lumen 4. The elongate shaft 5 comprises a first passageway, in this embodiment a channel 9, which extends axially therethrough from a forward opening 11 in a forward end 12 of the shaft 5 to a rearward opening 13 in a rearward end of the shaft 5. Hereby, the first passageway 8 in the forward section 5 communicates with the second passageway 4 in the rearward section 3. However, other ways of obtaining such a communication are possible. The first passageway, instead of or in addition to having a rearward opening debauching axially inside the second passageway, could have a lateral opening arranged inside the second passageway ahead of the rearward end, and hence debouching radially, or at least partly in a radial direction.

The forward portion 8 of the elongate shaft 5 is adapted for insertion into the anal canal of the patient, as will hereinafter be described. To this end, the forward portion of the shaft 5 is preferably provided with a coating which exhibits a reduced friction in use. Most preferably a coating which exhibits a reduced friction when wetted is used, e.g. the hydrophilic coating disclosed in EP-0 093 093 and EP-0 217 771 by the same applicant.

Further, it is preferred that the forward end 12 of the shaft 5 is enlarged. Hereby, a more efficient stimulation of the sphincter muscle is obtained when the forward section is introduced into the anal canal of the patient. The enlarged forward end preferably has a length in the range of 3–8 mm, and most preferably around 5 mm. These lengths are especially suitable when the device is intended for infants. For adults a suitable length could be in the range 12–20 mm, and preferably around 15 mm. Still further, it is preferred that the enlarged end constitutes a smooth transition to the shaft 5, and further presents a rounded forward end, in order to avoid discomfort for the user, and alleviate the risk of causing any harmful injuries.

Further, it is preferred that the first passageway is tapering towards the forward end of the forward section in the vicinity of the forward opening, making the forward opening the narrowest part of the first passageway. This contributes in alleviating the risk of causing injuries to the patient. Further, the risk of faeces clogging and blocking the passageway is diminished.

To this end, it is also advantageous to let the whole, or at least a substantial part of the first passageway be slightly tapering in the length direction towards the front end. Such an embodiment is illustrated in the FIGS. 4 and 5 in the drawings. Preferably the tapering is more accentuated adjacent to the forward opening, and less accentuated in the rest of the passageway. The whole or part of the external surface of the forward portion of the forward section may also be tapering towards the forward end.

Arranged on a mid-section of the outer surface of the tube element 3 is preferably a series of circumferential ribs 15 to assist an operator in gripping the device 1. To this end, it is also advantageous to let the rearward section be at least slightly tapering towards the mid-section.

In use of the device 1, the operator inserts the enlarged forward end 12 of the elongate shaft 5 into the anal canal of the patient until the tube element 3 abuts the anus. This is the operative position of the device 1. The abutment of the tube element 3 with the anus allows the length of the forward portion 8 of the elongate shaft 5 to be correct for the patient being treated, that is, so that the enlarged forward end 12 of the shaft 5 is positioned just past the external sphincter muscles at the entry point of the anal canal thereby enabling the sphincter muscles to be stimulated if need be and gastrointestinal gases and faeces to be discharged. With this in mind, the length of the forward portion 8 of the shaft 5, i.e. the length of the part protruding from the forward end of the rearward section, should for adults be at least 30 mm, and preferably in the range 40–50 mm, and most preferably around 45 mm. The same length for infants should be in the range of about 15–35 mm, and preferably in the range 20–30, and most preferably around 25 mm. The abutment also sees to that a too deep insertion of the forward section into the anal canal is avoided. Hereby, the device could be used without the risk of causing any harmful injuries to the user.

In an alternative embodiment (not shown) the length of the forward portion may be variable. Hereby, the length of the protruding part of the device could be adjusted to suit the intended user. For example this may be obtained by arranging the elongated shaft axially displaceably relative the rearward section. Alternatively, the rearward section may be extendable, making the forward end of the rearward section displaceable relative to the forward section.

It is also preferred that the forward section, or the elongate shaft 5, is more flexible than the rearward section, or the tube element 3. Hereby, the rearward section provides a good grip at the same time as a preferably pliable and non-harmful forward section for insertion into the anal canal is provided. This difference in flexibility could be obtained by suitable choice of dimensions and/or material thickness of the parts. However, it could also be obtained by using different materials in different parts of the device.

Once the device 1 is located in the operative position, the annulus 7 between the elongate shaft 5 and wall of the lumen 4 of the tube element 3 acts to channel into the lumen 4 of the tube element 3 faeces not discharged into the lumen 4 via the channel 9 in the elongate shaft 5. Further, the device preferably comprises means for collecting discharged faeces or gases. For example, a bag (not shown) secured to the tube element 3 as in WO99/30652 supra could be arranged to collect the faeces and gases discharged into the lumen 4 through the channel 9 and annulus 7. Alternately, the tube element 3 could have a sealed rear end so that the tube element 3 acts as a container for the faeces and gases. It is also conceivable to connect the discharge output to some type of per se known suction or evacuation device.

It will be understood that the invention has been illustrated by an exemplary embodiment and that the invention can be varied in many ways within the ambit of the appended claims. For instance, the rectal insertion device can be made from many other plastic materials besides Pebax™. It will further be understood that the inclusion in the claims of reference numerals from the Figures of drawings is for illustration and not to be construed as having a limiting effect on the claims.

The invention claimed is:

1. A rectal insertion device for the treatment of disorders of the digestive tract of a human or animal patient comprising:
   a forward section which in an operative position of the device is disposed in the anal canal of the patient;
   a first passageway which extends rearwardly in the device from a first forward opening in the forward section;
   a rearward section having a forward end which in the operative position is disposed extra-corporeally; and
   a second passageway which extends rearwardly in the device from a second forward opening in the forward end of the rearward section, said second forward opening in the operative position thereby acting to catch faeces discharged from the anal canal not caught in the first passageway,
   wherein the first passageway communicates with the second passageway.

2. A rectal insertion device for the treatment of disorders of the digestive tract of a human or animal patient, said device comprising:
   a forward section which is intended to be inserted into the anal canal of the patient;
   a first passageway which extends in the device from a first forward opening in the forward section;
   a rearward section having a forward end presenting a second forward opening intended to be extra-corporeally in use, said second forward opening being arranged rearwardly from the first forward opening, so that said second forward opening in the operative position thereby acts to catch faeces discharged from the anal canal not caught in the first passageway,
   wherein the first passageway is in communication with said second forward opening.

3. The rectal insertion device as claimed in claim 2, wherein the rearward section comprises a rearwardly extending, second passageway being connected to the second opening.

4. The rectal insertion device as claimed in claim 1, 2 or 3, wherein in an operative position of the device the forward end of the rearward section abuts with the anus of the patient.

5. The rectal insertion device as claimed in claim 1 or 3, wherein the first and second passageways are substantially co-axially arranged.

6. The rectal insertion device as claimed in claim 1, wherein the forward end of the rearward section has a transverse dimension greater than the transverse dimension of the forward section, the forward section extending forwardly from the forward end of the rearward section.

7. The rectal insertion device as claimed in claim 1, wherein the forward section and rearward section are co-axially arranged.

8. The rectal insertion device as claimed in claim 1, wherein the forward section is arranged parallel but radially displaced relative to the rearward section.

9. The rectal insertion device as claimed in claim 6, 7 or 8, wherein the second forward opening is in the form of an annular opening formed around the forward section.

10. The rectal insertion device as claimed in claim 1 or 2, wherein the first passageway has a rearward opening debouching inside the second passageway.

11. The rectal insertion device as claimed in claim 1, wherein the rearward section of the device comprises a tubular element having an open-ended axial lumen.

12. The rectal insertion device as claimed in claim 11, wherein the device comprises an elongate shaft having a forward portion which presents the forward section of the device and a rearward portion which extends rearwardly from the forward portion into the tubular element.

13. The rectal insertion device as claimed in claim 12, wherein the first passageway extends through essentially the whole elongate shaft.

14. The rectal insertion device as claimed in claim 13, wherein the first passageway has a rearward opening in the rearward portion of the elongate shaft.

15. The rectal insertion device as claimed in any one of claims 12 to 14, wherein the rearward portion of the elongate shaft is spaced from the inner wall of the tubular element.

16. The rectal insertion device as claimed in claim 15, wherein the elongate shaft is attached to the inner wall of the tubular element through one or more rib elements.

17. The rectal insertion device as claimed in claim 1, wherein the rearward section comprises a gripping portion for maneuvering the device.

18. The rectal insertion device as claimed in claim 1, wherein the forward section is more flexible than the rearward section.

19. The rectal insertion device intended for adults as claimed in claim 1, wherein the length of the forward section protruding from the forward end of the rearward section is at least 30 mm.

20. The rectal insertion device intended for infants as claimed in claim 1, wherein the length of the forward section protruding from the forward end of the rearward section is in the range of about 15 mm.

21. The rectal insertion device as claimed in claim 1, wherein the device further comprises means for collecting faeces discharged into at least one of the first and second forward openings.

22. The rectal insertion device as claimed in claim 21, wherein the means for collecting faeces comprises a collection receptacle.

23. The rectal insertion device as claimed in claim 21, wherein the means for collecting faeces comprises a rearwardly sealed passageway connected to the opening.

24. The rectal insertion device as claimed in claim 1, wherein the forward section presents a transversely enlarged forward end portion.

25. The rectal insertion device as claimed in claim 1, wherein the first passageway is tapering towards the forward end of the forward section, making the forward opening the narrowest part of the first passageway.

26. The rectal insertion device as claimed in claim 1, wherein the rearward section is at least slightly tapering towards a mid-section.

27. A method for treating disorders of the digestive tract of a human or animal patient, comprising the step of:

at least one time inserting a forward section of a device into the anal canal of the patient, said forward section comprising a first passageway which extends rearwardly in the device from a first forward opening in the forward section wherein the device is inserted into the anal canal into a position where a rearward section of the device abuts the anus with a forward end, said rearward section comprising a second passageway which extends rearwardly in the device from a second forward opening in the forward end of the rearward section so that said second forward opening in the operative position thereby acts to catch faeces discharged from the anal canal not caught in the first passageway, wherein the first passageway communicates with the second passageway.

* * * * *